US00PP22916P2

(12) United States Plant Patent
Trees

(10) Patent No.: US PP22,916 P2
(45) Date of Patent: Jul. 31, 2012

(54) ***MIMULUS* PLANT NAMED 'GEORGIE RED'**

(50) Latin Name: *Mimulus aurantiacus*
Varietal Denomination: Georgie Red

(75) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 13/134,207

(22) Filed: Jun. 1, 2011

Related U.S. Application Data

(60) Provisional application No. 61/402,183, filed on Aug. 25, 2010.

(51) Int. Cl.
*A01H 5/00* (2006.01)

(52) U.S. Cl. ..... Plt./454

(58) Field of Classification Search ..... Plt./454
See application file for complete search history.

*Primary Examiner* — Kent L Bell
(74) *Attorney, Agent, or Firm* — Audrey Charles

(57) ABSTRACT

A new and distinct cultivar of *Mimulus* plant named 'Georgie Red', characterized by its dark red-orange colored flowers, dark green-colored foliage, and moderately vigorous, upright-mounded growth habit, is disclosed.

1 Drawing Sheet

Latin name of genus and species of plant claimed: *Mimulus aurantiacus.*

Variety denomination: 'Georgie Red'.

CROSS-REFERENCE TO RELATED APPLICATIONS

This application claims priority from U.S. Application No. 61/402,183 filed on Aug. 25, 2010.

BACKGROUND OF THE INVENTION

The present invention relates to a new and distinct cultivar of *Mimulus* plant botanically known as *Mimulus aurantiacus* and hereinafter referred to by the cultivar name 'Georgie Red'.

The new cultivar originated in a controlled breeding program in Guadalupe, Calif. during January 2008. The objective of the breeding program was the development of *Mimulus* cultivars with attractive flower coloration and a moderately vigorous, upright-mounded growth habit.

The new *Mimulus* cultivar is the result of cross-pollination. The female (seed) parent of the new cultivar is the proprietary *Mimulus aurantiacus* breeding selection designated MIM-129, not patented, characterized by its dark burgundy-red colored flowers having a cream picotee edge, dark green-colored foliage, and vigorous, semi-upright growth habit. The male (pollen) parent of the new cultivar is the proprietary *Mimulus aurantiacus* breeding selection designated MIM-195, not patented, characterized by its dark bright-orange colored flowers, medium green-colored foliage, low growth vigor, and compact, upright growth habit. The new cultivar was discovered and selected as a single flowering plant within the progeny of the above stated cross-pollination during January 2009 in a controlled environment in Guadalupe, Calif.

Asexual reproduction of the new cultivar by terminal stem cuttings since January 2009 in Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Georgie Red' as a new and distinct cultivar of *Mimulus* plant:

1. Dark red-orange colored flowers;
2. Dark green-colored foliage; and
3. Moderately vigorous, upright-mounded growth habit.

Plants of the new cultivar differ from plants of the female and male parents primarily in flower color and growth vigor.

Of the many commercially available *Mimulus* cultivars, the most similar in comparison to the new cultivar is 'Valentine', not patented. However, in side by side comparisons, plants of the new cultivar differ from plants of 'Valentine' in at least the following characteristics:

1. Plants of the new cultivar have smaller leaves, as measured by leaf length and leaf width, than plants of 'Valentine';
2. Plants of the new cultivar have smaller corolla, as measured by vertical axis and horizontal axis, than plants of 'Valentine'; and
3. Plants of the new cultivar have a flower color different from plants of 'Valentine'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Georgie Red'. The plants were grown in 4-inch pots for 11 weeks in a greenhouse at West Chicago, Ill. Plants were given one pinch at transplant.

DETAILED BOTANICAL DESCRIPTION

Figure 1:
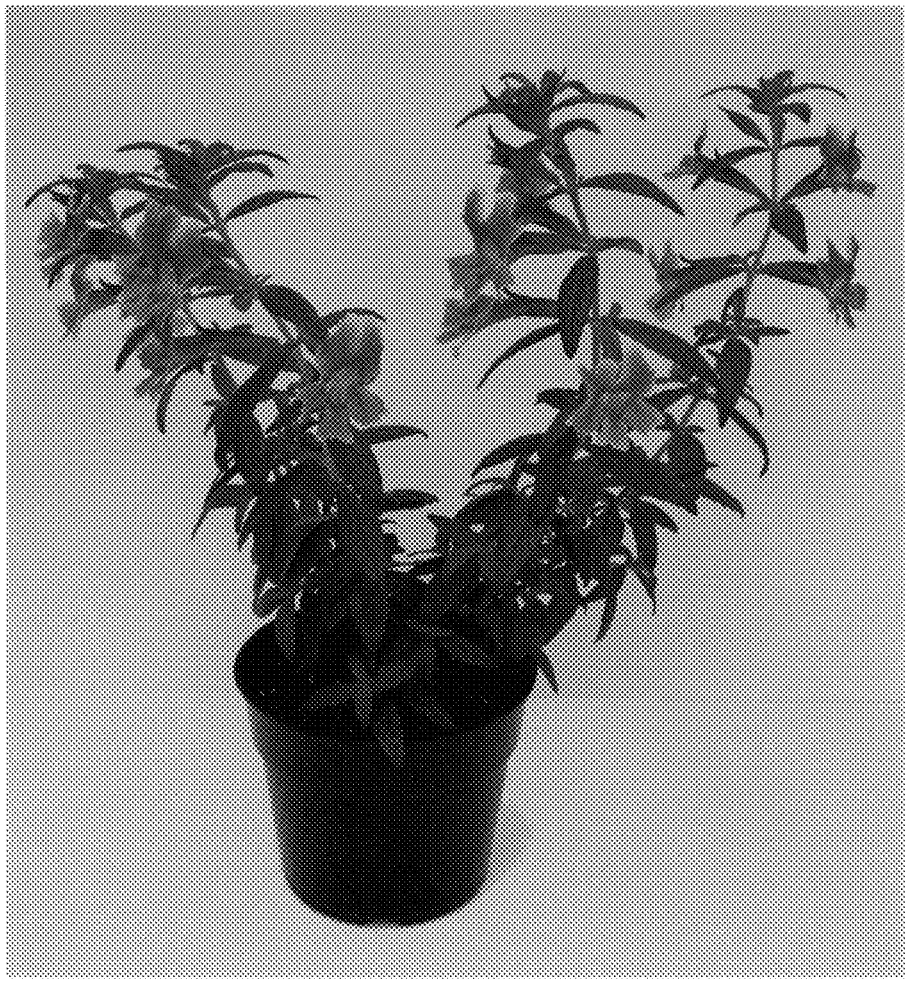
FIG. 1 illustrates a side view of the overall growth and flowering habit of 'Georgie Red'.
Figure 2:
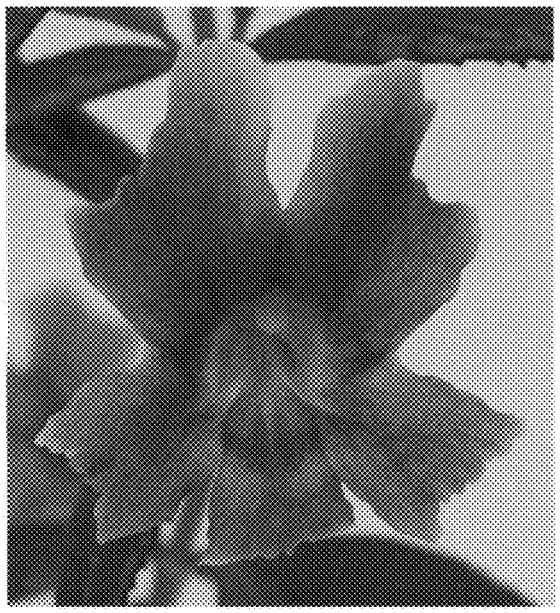
FIG. 2 illustrates a close-up view of an individual flower of 'Georgie Red'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in December 2010 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 11 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Mimulus aurantiacus* cultivar Georgie Red.

Parentage:

*Female parent*.—Proprietary *Mimulus aurantiacus* breeding selection designated MIM-129, not patented.

*Male parent*.—Proprietary *Mimulus aurantiacus* breeding selection designated MIM-195, not patented.

Propagation:

*Type cutting*.—Terminal stem.

*Time to initiate roots*.—Approximately 10 to 14 days.

*Time to produce a rooted cutting*.—Approximately 21 to 25 days.

*Root description*.—Fibrous.

*Rooting habit*.—Freely branching.

Plant description:

*Commercial crop time*.—Approximately 10 to 12 weeks from a rooted cutting to finish in a 10 cm pot.

*Growth habit and general appearance*.—Moderately vigorous, upright-mounded growth habit.

*Size*.—Height from soil level to top of plant plane: Approximately 28.8 cm. Width: Approximately 25.6 cm.

*Branching habit*.—Freely branching, pinching enhances basal branching. Quantity of main branches per plant: Approximately 4.

*Branch*.—Strength: Strong, somewhat flexible. Length: Approximately 22.1 cm. Diameter: Approximately 3.0 mm. Length of central internode: Approximately 2.3 cm. Texture: Glabrous, viscid, densely glandular pubescent. Color of young and mature stems: 145D.

Foliage description:

*General description*.—Quantity of leaves per main branch: Approximately 20. Fragrance: Slight. Form: Simple. Arrangement: Opposite.

*Leaves*.—Aspect: Perpendicular to stem, slightly reflexed. Shape: Elliptic. Margin: Serrate. Apex: Rounded acute. Base: Attenuate. Venation pattern: Pinnate. Length of mature leaf: Approximately 4.5 cm. Width of mature leaf: Approximately 1.6 cm. Texture of upper surface: Glabrous, glossy. Texture of lower surface: Glabrous, viscid, densely glandular pubescent. Color of upper surface of young foliage: 137A with indistinguishable venation. Color of lower surface of young and mature foliage: Closest to 138B with midvein of 147C. Color of upper surface of mature foliage: Darker than 137A with indistinguishable venation.

*Petiole*.—Length: Approximately 3.0 mm. Diameter: Approximately 3.0 mm. Texture: Glabrous, viscid, densely glandular pubescent. Color: 144C.

Flowering description:

*Flowering habit*.—'Georgie Red' is freely flowering under outdoor growing conditions with substantially continuous blooming from spring through autumn and year-round in greenhouse environment.

*Lastingness of individual flower on the plant*.—Approximately 2 to 3 weeks.

Flower description:

*General description*.—Type: Single, salverform, zygomorphic, axillary, facing outward. Quantity per plant: Approximately 11. Fragrance: None detected.

*Bud*.—Rate of opening: Generally takes 2 to 3 days for bud to progress from first color to fully open flower. Quantity per plant: Approximately 4.

*Bud just before opening*.—Shape: Elongate. Length: Approximately 2.7 cm. Diameter: Approximately 7.0 mm. Texture: Glabrous, slightly viscid, glandular pubescent. Color: Sepals of 144B with folded midvein area of 137A, petals of N170C.

*Corolla*.—Vertical axis: Approximately 3.8 cm. Horizontal axis: Approximately 3.3 cm.

*Lobes*.—Quantity: 5, fused to form a tube. Shape: Fan-shaped, upper two lobes reflexed. Margin: Irregularly sinuate and ruffled. Apex: Obtuse to truncate. Length from tube of upper two lobes: Approximately 2.1 cm. Length from tube of lower lobes: Approximately 1.1 cm. Width of upper two lobes: Approximately 1.7 cm. Width of lower lobes: Approximately 1.1 cm. Texture of upper and lower surfaces: Glabrous. Color of upper surface when first and fully open: 165D with a heavy overlay of N34A and 77A at throat opening. Color of lower surface when first and fully open: 161A with an overlay of N186C.

*Corolla tube*.—Length: Approximately 3.5 cm. Diameter at distal end: Approximately 8.0 mm. Diameter at proximal end: Approximately 2.0 mm. Texture of inner and outer surfaces: Glabrous. Color of inner surface: 76D with two nectar glides at base of lower lobe of 23A. Color of outer surface: N186D.

*Sepals*.—Quantity per flower: 5, fused. Shape: Elliptic, folded at midveins. Margin: Entire. Apex: Acute. Length: Approximately 2.5 cm with one upper sepal of approximately 3.0 cm. Width: Approximately 4.0 mm. Texture of upper and lower surfaces: Glabrous, slightly viscid, glandular pubescent. Color of upper and lower surfaces: 144B with folded midvein area of 137A.

*Peduncle*.—Strength: Strong, flexible. Aspect: Acute angle to stem. Length: Approximately 4.0 mm. Diameter: Approximately 1.0 mm. Texture: Densely glandular pubescent. Color: 144B.

*Reproductive organs*.—Androecium: Stamen quantity: 4, didynamous, basifixed. Stamen length of longer pair: Approximately 2.7 cm. Stamen length of shorter pair: Approximately 2.4 cm. Filament length of fixed portion: Approximately 1.4 cm. Filament color: 145D. Anther shape: Bilobed, ovoid. Anther length: Approximately 1.0 mm. Anther color: 1D. Pollen amount: Not observed. Gynoecium: Pistil quantity: 1 per flower. Pistil length: Approximately 3.2 cm. Stigma shape: Flattened, bilobed. Stigma length: Approximately 2.0 mm. Stigma color: 155D. Style length: Approximately 2.6 cm. Style color: 155A. Ovary length: Approximately 4.0 mm. Ovary color: 144A.

Seed and fruit production: Neither seed nor fruit production has been observed.

Disease and pest resistance: Resistance to pathogens and pests common to *Mimulus* has not been observed.

What is claimed is:

1. A new and distinct cultivar of *Mimulus* plant named 'Georgie Red', substantially as herein shown and described.

* * * * *